United States Patent [19]

Carr

[11] 4,164,576

[45] Aug. 14, 1979

[54] BENZOXAZINE CARBOXAMIDES

[75] Inventor: John B. Carr, Houston, Tex.

[73] Assignee: Shell Oil Company, Houston, Tex.

[21] Appl. No.: 933,336

[22] Filed: Aug. 14, 1978

Related U.S. Application Data

[63] Continuation-in-part of Ser. No. 889,759, Mar. 24, 1978, abandoned, which is a continuation-in-part of Ser. No. 778,816, Mar. 17, 1977, abandoned.

[51] Int. Cl.$^2$ .................. C07D 265/36; A61K 31/35
[52] U.S. Cl. .............................. 424/248.54; 544/105
[58] Field of Search ................ 544/105; 424/248.54; 260/244 R

[56] References Cited

U.S. PATENT DOCUMENTS

| | | | |
|---|---|---|---|
| 3,935,203 | 1/1976 | Thuillier et al. | 544/105 |
| 3,984,405 | 10/1976 | Krapcho | 544/105 |

FOREIGN PATENT DOCUMENTS 1057508  2/1967  United Kingdom ...................... 544/105

OTHER PUBLICATIONS

Predvoditeleva et al., Chem. Abstracts, vol. 58, col. 609 (1963).
Predvoditeleva et al., Chem. Abstracts, vol. 60, col. 9270–9271 (1964).

*Primary Examiner*—John D. Randolph

[57] ABSTRACT 3,4-Dihydro-N-(2-propenyl)-2H-1,4-benzoxazine-2-carboxamides, useful as lipogenesis inhibitors in mammals.

4 Claims, No Drawings

BENZOXAZINE CARBOXAMIDES

This application is a continuation-in-part of application Ser. No. 889,759, filed Mar. 24, 1978, abandon which was a continuation-in-part of application Ser. No. 778,816, filed on Mar. 17, 1977, abandoned.

DESCRIPTION OF THE INVENTION

It has been found that lipogenesis in mammals is inhibited by 3,4-dihydro-N-(2-propenyl)-2H-1,4-benzoxazine-2-carboxamides, which can be described by the formula

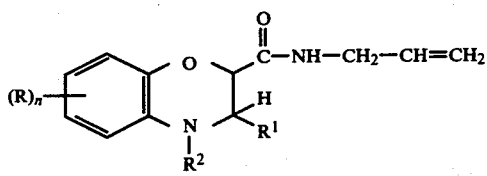

wherein n is zero, one or two, R is lower halogen, amino, methylsulfonylamino, trifluoromethyl, alkyl or alkoxy of from one to six carbon atoms, or phenyl; $R^1$ is hydrogen or alkyl of from one to four carbon atoms, and $R^2$ is hydrogen or alkyl of from one to four carbon atoms, with the proviso that when n is 2, the two moieties, R, are substituted on the carbon atoms at the 6- and 7-positions in the molecule. By lower halogen is meant chlorine, fluorine and bromine, chlorine being preferred. Each alkyl moiety may be of straight-chain or branched-chain configuration.

Preferred of these compounds, because of their activity in inhibiting lipogenesis, are those wherein n is zero or n is one and R is middle halogen, alkyl or trifluoromethyl, $R^1$ is hydrogen and $R^2$ is hydrogen or methyl.

Compounds of Formula I are basic in character, and form salts with acids, such as the hydrohalic acids, which are physiologically acceptable and are also effective inhibitors of lipogenesis in mammals. Such salts accordingly are included in this invention.

Those compounds of Formula I wherein $R^1$ is alkyl can exist in the form of cis- and trans- geometrical isomers, referring to the spatial relationship of the carboxamide and $R^1$-alkyl moieties. Further, chirality exists in the compounds due to the asymmetric structural configuration at the 2-position of the 3,4-dihydro-1,4-benzoxazine ring. As a result, two optical isomers of the compounds of Formula I wherein $R^1$ is hydrogen exist, while in those compounds wherein $R^1$ is alkyl, four optical isomers exist, one pair for each of the two geometrical isomers. At the time this application is filed, no attempt has been made to separate and determine the lipogenesis inhibition activity of the individual geometrical and optical isomers. Under the circumstances, the invention contemplates the active individual geometrical and optical isomers, as well as mixtures thereof.

For illustration, preparation of typical individual species of the genus defined by Formula I is described in the examples included hereinafter. Other typical, illustrative individual species of the genus include those wherein the respective moieties are:

$R^1$ is hydrogen, $R^2$ is hydrogen, n is one,
R is:
6-amino;
6-bromo;
5-chloro;

$R^1$ is methyl, $R^2$ is hydrogen, n is zero;
$R^1$ is methyl, $R^2$ is methyl, n is zero;
$R^1$ is hydrogen, $R^2$ is butyl, n is zero;
$R^1$ is hydrogen, $R^2$ is isopropyl, n is 1, R is 6-chloro;
$R^1$ is hydrogen, $R^2$ is ethyl, n is 1, R is 6-bromo;
$R^1$ is hydrogen, $R^2$ is isobutyl, n is 1, R is 6-methyl;
$R^1$ is propyl, $R^2$ is hydrogen, n is 1, R is 6-chloro;
$R^1$ is hydrogen, $R^2$ is hydrogen, n is 2,
R is:
6-chloro, 7-methyl;

Compounds of this genus can be prepared by treating an alkyl, suitably methyl or ethyl, ester of the corresponding carboxylic acid, in solution in a suitable solvent such as ethanol, with 2-propenamine. The reaction will go forward at room temperature; however, higher temperatures—for example, the mixture can be refluxed—may be employed to reduce the reaction time. Preferably, about a four-to-six fold excess of the amine is used. The desired product can be recovered by evaporating the solvent and excess amine, then employing conventional techniques such as selective extraction, recrystallization and/or dry column chromatography, to isolate the desired product. Use of these procedures in particular instances is illustrated in the working examples included hereinafter.

The ethyl ester of 3,4-dihydro-2H-1,4-benzoxazine-2-carboxylic acid is a known compound: British Pat. No. 1,057,568. Other precursor esters wherein $R^1$ is alkyl can be prepared by condensing a methyl or ethyl ester of the appropriate 2,3-dibromo-butyric, pentanoic or hexanoic acid with the appropriate 4-R-2-aminophenol in the presence of a base such as potassium carbonate, in a solvent such as acetone, at or somewhat above room temperature. Some of the precursor phenols (R=H, chlorine, methyl, methoxy) are known; methods for preparing others are shown in the Examples, hereinafter, and by Katz et al., J. Org. Chem., 19, 758 (1954).

Those species wherein R is methylsulfonylamino can be prepared by treating the species wherein R is amino with methanesulfonyl chloride, as shown in Example 6.

Example 2 demonstrates a general procedure for preparing the precursor esters for species wherein $R^2$ is alkyl, by the sequential treatment of a dimethylformamide solution of the appropriate ester with thallium ethoxide and the appropriate alkyl halide ($R^2$-halogen).

The procedures for preparing compounds of Formula I are illustrated in the following examples. In each case, the identities of the product, and of the precursor(s) involved, were confirmed by appropriate chemical and spectral analyses.

EXAMPLE 1

3,4-dihydro-N-(2-propenyl)-2H-1,4-benzoxazine-2-carboxamide (1)

3,4-Dihydro-2H-1,4-benzoxazine-2-carboxylic acid ethyl ester, hydrochloride (1A) was prepared as white crystals, mp: 186°–188° C. (British Pat. No. 1,057,568: mp: 181°–185° C.) by the potassium carbonate mediated condensation of o-aminophenol and ethyl 2,3-dibromopropionate in dry acetone according to the procedure shown in British Pat. No. 1,057,568. 1A was treated with sodium bicarbonate to prepare the free base (1B).

A solution of 7.3 g of (1B) and 6.84 g of 2-propenamine in 50 ml of ethanol was stirred at room temperature for 3 days. Then solvent and excess amine were stripped off and the residue was partitioned between ether and water. The ether layer was separated and the aqueous layer was extracted with ether. The ether solutions were combined, washed with water, dried (MgSO₄), and concentrated to give 1, as white crystals, mp: 90°–91° C.

EXAMPLE 2

3,4-dihydro-4-methyl-N-(2-propenyl)-2H-1,4-benzoxazine-2-carboxamide (2)

To a stirred solution of 2.6 g of (1B) in 50 ml of ethanol was added dropwise at room temperature a solution of 3.76 g of thallium ethoxide in 50 ml of ethanol. The resulting mixture was stirred at room temperature for 24 hours. Then a solution of 1.8 g of methyl iodide in 50 ml of dimethylformamide was added and the resulting mixture was stirred at room temperature for 72 hours. The mixture then was filtered and the solvent was stripped from the filtrate to leave a gum. This product was refluxed overnight in ethanol containing a small amount of sulfuric acid as catalyst. The resulting mixture was cooled and neutralized with sodium bicarbonate; the solvent was stripped off and the residue was partitioned between water and methylene chlorine. The methylene chloride layer was separated; the aqueous layer was extracted with methylene chloride; the methylene chloride solutions were combined, washed with water, dried (MgSO₄) and the solvent was stripped off to give a liquid residue. The residue was dry column chromatographed through silica gel, using Solvent No. 3 (a 4:30:66 by volume mixture of tetrahydrofuran, ethyl acetate and hexane) as eluent. On workup, the faster-moving, major component was separated, dissolved in ether and treated with hydrogen chloride gas, to form the hydrochloride salt, as a gum. The gum was separated and triturated with ethanol and the resulting solution was cooled to give the hydrochloride salt of the ethyl ester of 3,4-dihydro-4-methyl-2H-1,4-benzoxazine-2-carboxylic acid (2A) as white crystals, mp; 89°–93° C.

A solution of 1.1 g of 2A, and 5 ml of 2-propenamine in 25 ml of ethanol was refluxed for 16 hours. The solvent and excess amine were stripped off and the residue was passed through a silica gel column using Solvent No. 3 as eluent. The solvent was stripped off to give 2, as light yellow liquid, boiling point not determined.

EXAMPLE 3

6-chloro-3,4-dihydro-N-(2-propenyl)-2H-1,4-benzoxazine-2-carboxamide (3)

43.0 g of 2-amino-4-chlorophenol was dissolved in 500 ml of anhydrous acetone containing 42.0 g of anhydrous potassium carbonate. That mixture was heated to reflux temperature and 23.0 g of ethyl 2,3-dibromopropionate was added dropwise. In three additional portions each, additional ester and carbonate were added to the refluxing mixture until a total of 124 g of carbonate and 85.8 g of ester had been added. The mixture was refluxed for 21 hours. Solids were filtered from the mixture and washed with acetone. The filtrate was stripped of solvent and the residue was taken up in water. The water solution was extracted with ether. The ether extract was dried (MgSO₄) and the solvent was stripped. The residue was eluted through a silica gel column using Solvent No. 3, the solvent was stripped and the residue was recrystallized from ethanol, then from ether to give ethyl 6-chloro-3,4-dihydro-2H-1,4-benzoxazine-2-carboxylate (3A), as white crystals, mp; 85.5°–86.5° C.

3 was prepared as white platelets, mp: 114°–114.5° C., by treating 3A with 2-propenamine by the procedure of Example 1.

EXAMPLE 4

6-methyl-3,4-dihydro-N-(2-propenyl)-2H-1,4-benzoxazine-2-carboxamide (4)

29.3 g of ethyl 2,3-dibromopropionate was added over a ten minute period to a refluxing mixture of 19.0 g of anhydrous potassium carbonate, 56.6 g of 2-amino-p-cresol and 500 ml of dry acetone. The ethyl 2,3-dibromopropionate and potassium carbonate addition was repeated thrice to give a total of 76 g of potassium carbonate and 118 g of ethyl 2,3-dibrompropionate. The mixture then was refluxed for 17 hours, filtered and the filtrate was stripped of solvent under reduced pressure. The liquid residue was diluted with 300 ml of 1 N sodium hydroxide solution at 5°–10° C., then extracted four times with 300 ml portions of ether. The extracts were combined, dried (MgSO₄) and treated with hydrogen chloride gas at 5°–10° C. A solid which formed was filtered and extracted with acetone. The residue was recrystallized from ethanol to give the ethyl ester of 6-methyl-3,4-dihydro-2H-1,4-benzoxazine-2-carboxylic acid hydrochloride (4A), as white crystals, mp: 158°–160° C.

42.4 g of 4A and 38 g of 2-propenamine were mixed in 165 ml of ethanol and the mixture was stirred at room temperature for 90 hours. The solvent was removed under reduced pressure. The residue was partitioned between ether and water. The ether solution was dried (MgSO₄), about half the solvent was evaporated, and solid which formed was filtered, then dried under reduced pressure to give 4, mp: 113°–115° C.

EXAMPLE 5

3,4-dihydro-6-((methylsulfonyl)amino)-N-(2-propenyl)-2H-1,4-benzoxazine-2-carboxamide (5)

29.2 g of ethyl 2,3-dibromopropionate was added dropwise to a refluxing mixture of 19 g of anhydrous potassium carbonate, 70.9 g of 4-nitro-2-aminophenol and 500 ml of dry acetone. The ethyl 2,3-dibromopropionate and potassium carbonate addition was repeated thrice to give a total of 76 g of potassium carbonate and 118 g of ethyl 2,3-dibromopropionate. The reaction mixture was refluxed for 17 hours, then filtered. The filtrate was concentrated under reduced pressure. The residue was washed with dilute sodium hydroxide solution then was extracted with ether and with methylene chloride. The solvents were evaporated. Thin layer chromatographic analyses indicated that both products were the same. They were combined and recrystallized from ether to give the ethyl ester of 6-nitro-3,4-dihydro-2H-1,4-benzoxazine-2-carboxylic acid (5A), as a solid, mp: 88°–90° C.

Two 1-gram portions of 10% palladium-on-carbon catalyst were added to 10 g of 5A in 700 ml of ethanol. The mixture was hydrogenated at 50 psig for 2 hours. Fresh catalyst was added and the mixture again was hydrogenated. This procedure was repeated four times, when thin layer chromatographic analysis indicated that the nitro moiety had been completely converted to the amino moiety. The reaction mixture was filtered and the filtrate was concentrated to give the amino derivative (5B) as a brown liquid.

A mixture of 14.7 g of 5B and 7.3 g of triethylamine in 200 ml of methylene chloride was treated with 8.3 g of methanesulfonyl chloride at 0°–5° C. The mixture was stirred for 2 hours, washed with water, dried, filtered, and the solvent was evaporated. The residue was washed with a small amount of ethanol, filtered, and recrystallized from ethanol to give the methylsulfonylamino derivative (5C), as a solid, mp: 149°–151° C.

A mixture of 7.3 g of 5C, 20 ml of 2-propenamine and 10 ml of ethanol was stirred at room temperature for 20 hours. The solid product was filtered, dried and recrystallized from ethanol/acetone, (6/1 v/v) to give 5, as white crystals, mp: 178°–180° C.

EXAMPLE 6

6-(trifluoromethyl)-3,4-dihydro-N-(2-propenyl)-2H-1,4-benzoxazine-2-carboxamide (6)

87.6 g of finely powdered sodium hydroxide was added in portions over an 8-hour period to a stirred solution of 165.0 g of 2-nitro-4-(trifluoromethyl)chlorobenzene in 220 ml of dimethyl sulfoxide at room temperature. The mixture was allowed to stand overnight, then poured into 1.5 liters of cold water. The resulting mixture was acidified to pH 1 with concentrated hydrochloric acid. An oil formed; it was separated and dissolved in ether. The solution was dried ($MgSO_4$) and stripped of solvent under reduced pressure. The residue was mixed with cold sodium hydroxide solution and the mixture was extracted with petroleum ether. The water layer was acidified with concentrated hydrochloric acid. The resulting oil was separated and dissolved in ether. The solution was dried ($MgSO_4$) and stripped of solvent to give 2-nitro-4-(trifluoromethyl)phenol (6A).

82.2 g of 6A was dissolved in 300 ml of ethanol. 0.5 g of platinum oxide catalyst was added and the mixture was hydrogenated at 50 psig. Fresh portions of catalyst were added periodically. The reaction mixture was filtered, and the filtrate was concentrated. The residue was crystallized from water to give 2-amino-4-(trifluoromethyl)phenol (6B).

11.4 g of potassium carbonate was added to 48.7 g of 6B in 320 ml of acetone. Then 18.2 g of ethyl 2,3-dibromopropionate was added dropwise to the refluxing mixture. The ethyl 2,3-dibromopropionate and potassium carbonate addition was repeated thrice, to give a total of 45.6 g of potassium carbonate and 72.8 g of ethyl 2,3-dibromopropionate. The reaction mixture then was refluxed for 17 hours and filtered, and the filtrate was stripped of solvent under reduced pressure. The residue was dissolved in ether; the solution was washed with dilute sodium hydroxide solution, then dried ($MgSO_4$) and stripped of solvent. The residue was washed with petroleum ether, dried and dissolved in ether. The ether solution was partially concentrated and cooled. The resulting crystals were filtered and recrystallized from ether to give the ethyl ester of 6-trifluoromethyl-3,4-dihydro-2H-1,4-benzoxazine-2-carboxylic acid (6C) mp: 105°–107° C.

A mixture of 20.6 g of 6C, 25.7 g of 2-propenamine and 34 ml of ethanol was stirred at room temperature for 36 hours. The excess amine and solvent were evaporated under reduced pressure. The solid residue was mixed with 150 ml of ether and the remaining solid material was filtered. The filtrate was added to petroleum ether and cooled; the resulting viscous material was filtered. The filtrate was stripped and the residue was triturated with petroleum ether to give an off-white powder which was purified by dry-column chromatography (silica gel), using ether as eluent. The higher Rf band was collected and extracted with ether, the solvent was stripped and the solid residue was recrystallized from ether/hexane (4/5 v/v). Thin-layer chromatography indicated that two components were present. The product was purified by wet-column chromatography (silica gel) using petroleum ether/ethyl ether (1:4 v/v) as eluent. The solvent was stripped and the residue was recrystallized from ether/hexane (75:100 v/v) to give 6, as a solid, mp: 95°–97° C.

EXAMPLE 7

3,4-dihydro-6-methoxy-N-(2-propenyl)-2H-1,4-benzoxazine-2-carboxamide (7)

336.4 g of 2-nitro-4-methoxyaniline was refluxed with 200 g of sodium hydroxide and 10 g of arsenic trioxide in 6500 ml of water, for 20 hours. The resulting solution was cooled on an ice-bath, acidified to pH 1 with concentrated hydrochloric acid and filtered. The solid product was washed with water, and dried under vacuum and in the presence of $P_2O_5$ to give 4-methoxy-2-nitrophenol (7A), mp: 78°–80° C.

193.1 g of 7A was mixed with 1400 ml of water. 513 ml of ammonium hydroxide was added. 595 g of powdered sodium dithionite was added in portions over a period of 50 minutes. The resulting mixture was stirred for 2 hours. The solid product was collected and dried under vacuum over $P_2O_5$ to give 4-methoxy-2-aminophenol (7B), mp: 134°–136° C.

7B was treated with ethyl 2,3-dibromopropionate to form the ethyl ester of 6-methoxy-3,4-dihydro-2H-1,4-benzoxazine-2-carboxylic acid, and this was converted to 7, mp: 83°–85° C., by the procedures described in the other examples.

EXAMPLES 8 and 9

The required precursor phenols were prepared from known substituted benzenes by procedures described in the preceding examples, and were converted, by procedures described in those examples to:

8-chloro-3,4-dihydro-N-(2-propenyl)-2H-1,4-benzoxazine-2-carboxamide (8), mp: 65°–66° C. and
6,7-dichloro-3,4-dihydro-N-(2-propenyl)-2H-1,4-benzoxazine-2-carboxamide (9), mp: 82°–84° C.

EXAMPLES 10–11

By the procedures described in the preceding examples, there were prepared from known phenols:

3,4-dihydro-7-methyl-N-(2-propenyl)-2H-1,4-benzoxazine-2-carboxamide (10), mp: 89°–91° C.
3,4-dihydro-6-phenyl-N-(2-propenyl)-2H-1,4-benzoxazine-2-carboxamide (11), mp: 120°–122° C.

The carboxamides of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the up-take of the radio-active carbon by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Rringer bicarbonate solution containing one-half the normal calcium ion concentration, 60 micromoles of glucose, 0.5 micro-Curie of glucose-U$^{14}$C, and 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1 v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compounds in each case. The data obtained from the tests are set out in Table 1, as the percent inhibition of lipogenesis compared to the results obtained in the control tests wherein only the test compound was omitted.

Table I

| Compound No. | Percent Inhibition |
|---|---|
| 1 | 51 |
| 2 | 40 |
| 3 | 63 |
| 4 | 57 |
| 5 | 40 |
| 6 | 57 |
| 7 | 76 |
| 8 | 24 |
| 9 | 44 |
| 10 | 21 |
| 11 | 70 |

The carboxamides of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the carboxamides orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboxamide used, and the particular animal being treated. However, in general, satisfactory results are obtained when the carboxamides are administered in a dosage of from about 1 to about 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used as the inhibitor, and the professional judgment of the person administering or supervising the administration of the inhibitor. It is to be understood that the dosages set forth herein are exemplary only, and that they do not, to any extent, limit the scope or practice of the invention.

I claim as my invention:

1. A compound of the formula

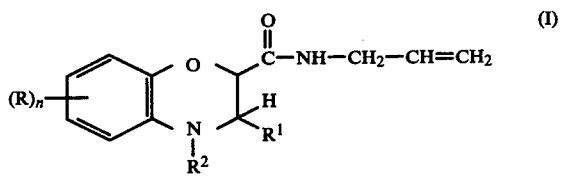

wherein n is zero, one or two, R is lower halogen, amino, methylsulfonylamino, trifluoromethyl, alkyl or alkoxy of from one to six carbon atoms, or phenyl; R$^1$ is hydrogen or alkyl of from one to four carbon atoms, and R$^2$ is hydrogen, or alkyl of from one to four carbon atoms, and hydrohalic acid salts thereof, with the proviso that when n is 2, the two moieties, R, are substituted on the carbon atoms at the 6- and 7-positions in the molecule.

2. A compound according to claim 1 wherein n is zero, or n is one and R is middle halogen, alkyl or trifluoromethyl, R$^1$ is hydrogen and R$^2$ is hydrogen or methyl.

3. A method of inhibiting lipogenesis in a mammal, which comprises administering, to a mammal in need of such treatment, orally or parenterally an effective amount of a compound of claim 1.

4. A method according to claim 3 wherein n is zero, or n is one and R is middle halogen, alkyl or trifluoromethyl, R$^1$ is hydrogen and R$^2$ is hydrogen or methyl.

* * * * *